US009182358B2

(12) United States Patent
Xu et al.

(10) Patent No.: US 9,182,358 B2
(45) Date of Patent: Nov. 10, 2015

(54) MULTI-SPOT DEFECT INSPECTION SYSTEM

(71) Applicant: KLA-Tencor Corporation, Milpitas, CA (US)

(72) Inventors: Zhiwei Xu, Sunnyvale, CA (US); Christian Wolters, San Jose, CA (US); Juergen Reich, Campbell, CA (US); Bret Whiteside, Gilroy, CA (US); Guoheng Zhao, Palo Alto, CA (US); Jijen Vazhaeparambil, Saratoga, CA (US); Stephen Biellak, Sunnyvale, CA (US); Sam Shamouilian, San Jose, CA (US); Mehdi Vaez-Iravani, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 36 days.

(21) Appl. No.: 13/834,662

(22) Filed: Mar. 15, 2013

(65) Prior Publication Data
US 2014/0268118 A1     Sep. 18, 2014

(51) Int. Cl.
*G01N 21/00*     (2006.01)
*G01N 21/95*     (2006.01)
*G01N 21/956*     (2006.01)

(52) U.S. Cl.
CPC .......... *G01N 21/9501* (2013.01); *G01N 21/956* (2013.01)

(58) Field of Classification Search
CPC . G01N 21/956; G01N 21/9501; G01N 21/94; G01N 21/8806; G01N 21/95607; H01L 22/12
USPC ............................................ 356/237.2–237.6
See application file for complete search history.

(56) References Cited

U.S. PATENT DOCUMENTS

| | | | | |
|---|---|---|---|---|
| 4,719,357 | A | * | 1/1988 | Ayata et al. .................... 250/548 |
| 5,751,403 | A | * | 5/1998 | Mizutani et al. ................ 355/53 |
| 6,731,384 | B2 | * | 5/2004 | Ohshima et al. ........... 356/237.2 |
| 8,194,301 | B2 | | 6/2012 | Zhao et al. |
| 2001/0048521 | A1 | * | 12/2001 | Vaez-Iravani .............. 356/237.2 |
| 2005/0052644 | A1 | * | 3/2005 | Lewis et al. ................ 356/237.4 |
| 2005/0165386 | A1 | | 7/2005 | Kurtz et al. |
| 2007/0153265 | A1 | * | 7/2007 | Vaez-Iravani et al. ..... 356/237.5 |
| 2009/0225399 | A1 | * | 9/2009 | Zhao et al. ..................... 359/298 |
| 2012/0026489 | A1 | | 2/2012 | Zhao et al. |
| 2012/0229802 | A1 | | 9/2012 | Wolters et al. |
| 2012/0235016 | A1 | | 9/2012 | Weiner et al. |
| 2013/0050689 | A1 | * | 2/2013 | Reich et al. ................ 356/237.4 |

FOREIGN PATENT DOCUMENTS

JP     2000-260376 A     9/2000

* cited by examiner

*Primary Examiner* — Tarifur Chowdhury
*Assistant Examiner* — Isiaka Akanbi
(74) *Attorney, Agent, or Firm* — Suiter Swantz pc llo

(57) ABSTRACT

The disclosure is directed to a system and method for inspecting a spinning sample by substantially simultaneously scanning multiple spots on a surface of the sample utilizing a plurality of illumination beams. Portions of illumination reflected, scattered, or radiated from respective spots on the surface of the sample are collected by at least one detector array. Information associated with at least one defect of the sample is determined by at least one computing system in communication with the detector array. According to various embodiments, at least one of scan pitch, spot size, spot separation, and spin rate is controlled to compensate pitch error due to tangential spot separation.

31 Claims, 7 Drawing Sheets

MULTI-SPOT DEFECT INSPECTION SYSTEM

TECHNICAL FIELD

The present disclosure generally relates to the field of sample inspection and more particularly to performing multi-spot inspection on a spinning sample.

BACKGROUND

Several defect inspection systems are known in the art, typically relying on a single-spot scan of a sample surface. Scanning the sample with a single illumination beam is appropriate in many applications. However, emerging technologies constantly require higher sampling rates and defect sensitivity than single-spot inspections systems are capable of providing. Accordingly, multi-spot inspection systems have been proposed to improve throughput and sensitivity by substantially simultaneously scanning the sample with a plurality of illumination beams and processing the resulting scan information in parallel.

The multi-spot inspection systems currently known to the art suffer from various complexities. For example, pitch error is a prevalent problem is multi-spot scans of a spinning wafer. Radially spaced spot patterns are less prone to pitch error because a tilt angle between spot path and scan direction is avoided. However, radial spot patterns present are difficult to generate and will typically require a much more complex optical designs than those required for generating tangential spot patterns.

SUMMARY

In one aspect, the disclosure is directed to multi-spot inspection system for determining information (e.g. location, size, classification) associated with at least one defect of a sample. The system may include a stage assembly configured to support a sample and further configured to spin the sample utilizing at least one rotating actuator. At least one illumination source is configured to provide illumination along an illumination path to a surface of the spinning sample. A spot array generator disposed along the illumination path is configured to direct portions of illumination according to a selected pattern (e.g. radial or tangential spacing) to illuminate a plurality of spots on the surface of the sample. At least one detector array is configured to receive illumination reflected, scattered, or radiated from the plurality of spots on the surface of the sample. At least one computing system is configured to determine information associated with at least one defect of the sample based upon the illumination received by detector array.

According to various embodiments, scan pitch, spot size, spot separation, and/or spin rate may be controlled to compensate pitch error due to tangential spot separation. In some embodiments, for example, the stage assembly further includes at least one lateral actuator configured to actuate the sample along at least one axis to control scan pitch of the portions of illumination directed at the surface of the sample. The lateral actuator may be configured to vary the scan pitch across multiple regions of the sample to compensate pitch error. Additional configurations and methods for compensating pitch error are further discussed in the detailed description that follows.

In another aspect, the disclosure is directed to a method of inspecting a sample in accordance with the system described herein. It is noted, however, that one or more steps of the method may be executed utilizing means beyond those described with regard to embodiments of the system. The method should be construed as broadly encompassing any means for carrying one or more of the steps described below. According to various embodiments, the method includes at least the steps of: directing portions of illumination according to a selected pattern to illuminate a plurality of spots on a surface of a spinning sample; receiving illumination reflected, scattered, or radiated from the plurality of spots on the surface of the sample; determining information associated with at least one defect of the sample based upon the illumination received from the surface of the sample; and controlling at least one of scan pitch, spot size, spot separation, and spin rate to compensate pitch error due to tangential spot separation.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1A through 6B generally illustrate a system and method for performing multi-spot inspection on a spinning sample. Scanning a sample with a plurality of laser spots can significantly improve sensitivity at fixed throughput. For example, the Signal-Noise-Ratio (SNR) can be shown to be proportional to $1/\sqrt{n}$, in first order, where n is number of laser spots.

Increasing the number of laser spots used to scan the sample may lead to various complexities. For example, number of detector sensors (e.g. photomultiplier tubes) is typically proportional to the number of laser spots so hardware layout may become more complex as the number of spots is increased. Very stable intensity amplitude ratio between various spots must be maintained. Since S/N scales with square root of n, increase of laser spots will eventually reach a point of diminishing of returns when n is large enough. In some embodiments, the number of spots (n) is selected based upon the foregoing considerations.

Figure 1A:
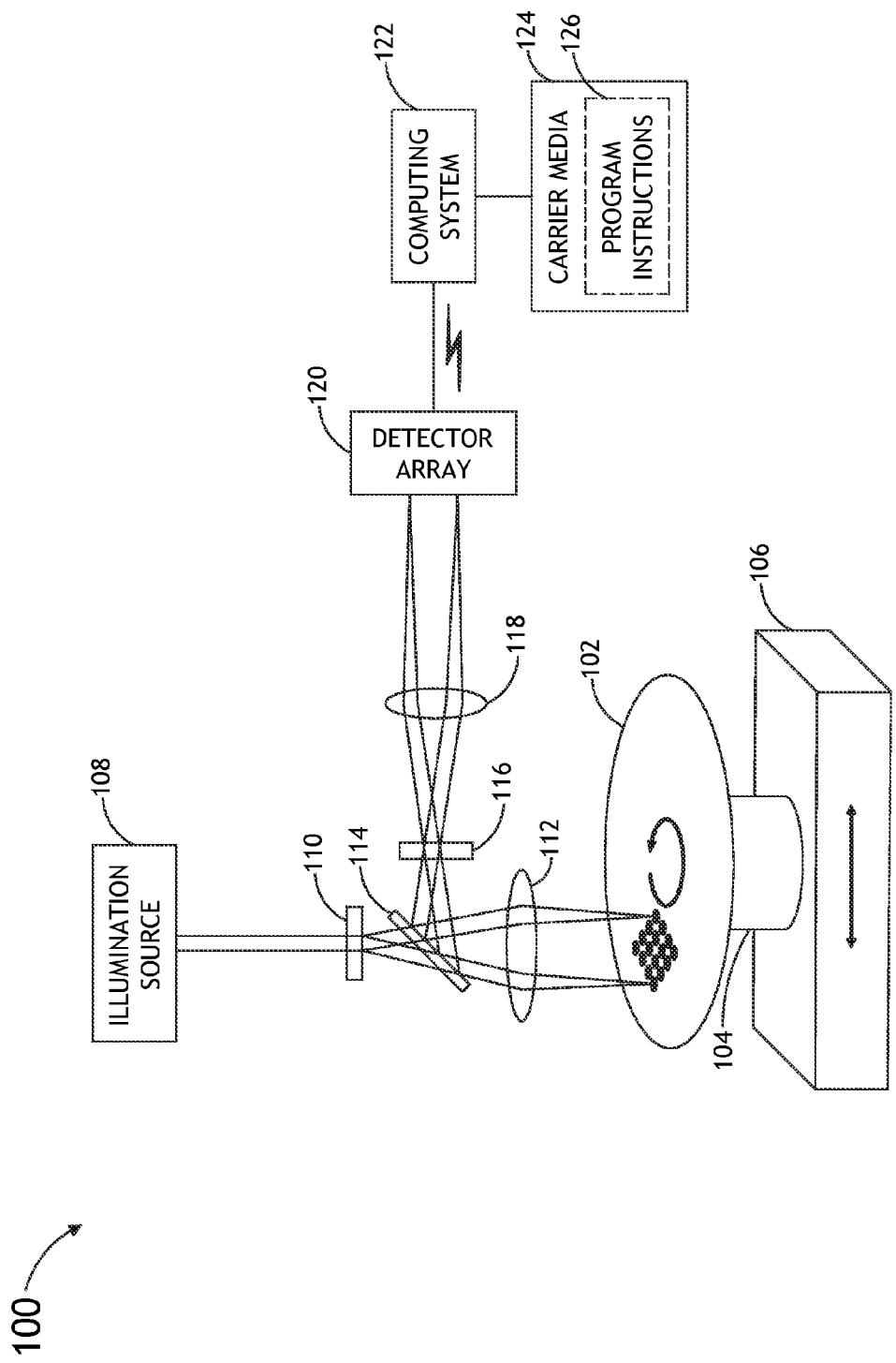
FIG. 1A is a block diagram illustrating a multi-spot inspection system, in accordance with an embodiment of this disclosure.

FIG. 1A illustrates an embodiment of a system 100 for performing multi-spot inspection on a sample 102. As used throughout the present disclosure, the term "sample" generally refers to a substrate formed of a semiconductor or non-semiconductor material which may include one or more "layers" or "films" formed thereon. For example, semiconductor or non-semiconductor materials include, but are not limited to, monocrystalline silicon, gallium arsenide, and indium phosphide. Layers formed on the substrate may include, but are not limited to, a resist, a dielectric material, a conductive material, or a semiconductive material. Many different types of sample layers are known in the art, and the term sample as used herein is intended to encompass a substrate and any types of layers which may be formed thereon.

The system 100 may include a stage assembly configured to support a sample 102. The stage assembly may include at least one rotating actuator 104 (e.g. motor or servo) configured to spin the sample 102 according to a selected spin rate. The stage assembly may further include at least one lateral actuator 106 configured to linearly actuate the sample 102 along at least one axis (e.g. X-axis). The rotating actuator 104 and the linear actuator 106 may be configured to operate in concert such the sample 102 is spun at a selected spin rate while being linearly actuated in a selected direction. Thus, illumination impinging upon a surface of the sample 102 is enabled to scan the sample 102 according to a spiraling trajectory moving outwardly from (or inwardly to) the center of the sample 102.

At least one illumination source 108 is configured to provide illumination along an illumination path defined by one or more illumination optics 112, such as an objective lens. The illumination path may include a spot array generator 110 configured to receive illumination emanating from the illumination source 108 and further configured to direct separate portions (i.e. beams) of the illumination along the remainder of the illumination path according to a selected one-dimensional or two-dimensional spot pattern (e.g. radially or tangentially spaced array of spots). The spots may be spaced according to at least a threshold spot-to-spot separation to avoid cross talk between spots of illumination scanning the sample 102. In some embodiments, the spot array generator 110 includes a diffractive optical element (DOE) configured to diffract an illumination beam received from the illumination source 108 to generate the spot pattern utilized to illuminate the surface of the sample 102. U.S. Pat. No. 8,194,301, US Pub. No. 2009/0225399, and US Pub. No. 2012/0026489 discuss methods of generating and/or using multi-spot arrays in further detail, and are all incorporated herein by reference.

The lateral actuator 106 is configured to actuate the sample 102 so that the spot pattern is scanned along the sample surface. Meanwhile, at least one detector array 120 is configured to receive portions of illumination reflected, scattered, or radiated from the sample surface along a collection path defined by one or more collection optics such as, but not limited to, a beam splitter 114, an aperture or Fourier filter 116, and an imaging lens 118. The detector array 120 may include a plurality of photomultiplier tubes (PMTs), cameras, or any other array of photo-sensors known to the art.

The system 100 further includes at least one computing system 122 communicatively coupled to the detector array 120. In some embodiments, the computing system 122 is configured to independently or at least partially independently process a portion of received illumination for each of the respective illumination beams (i.e. illumination reflected, scattered, or radiated from each spot). For example, the computing system 122 may be configured to digitize data from each illuminated spot of the sample surface independently and then combine the digitized data for defect detection. The computing system 122 is configured to determine information (e.g. location, size, classification) associated with one or more defects of the sample 102 based upon illumination reflected, scattered, or radiated from the plurality of illuminated spots. Accordingly, defect sensitivity and throughput may be substantially increased in relation to the number (n) of spots illuminating the surface of the sample 102.

It should be recognized that the various steps and functions described throughout the present disclosure may be carried out by a single computing system or by multiple computing systems. The one or more computing systems 122 may include, but are not limited to, a personal computing system, mainframe computing system, workstation, image computer, parallel processor, or any other device known in the art. In general, the term "computing system" may be broadly defined to encompass any device having at least one single-core or multiple-core processor configured to execute program instructions 126 from at least one carrier medium 124.

Figure 1B:
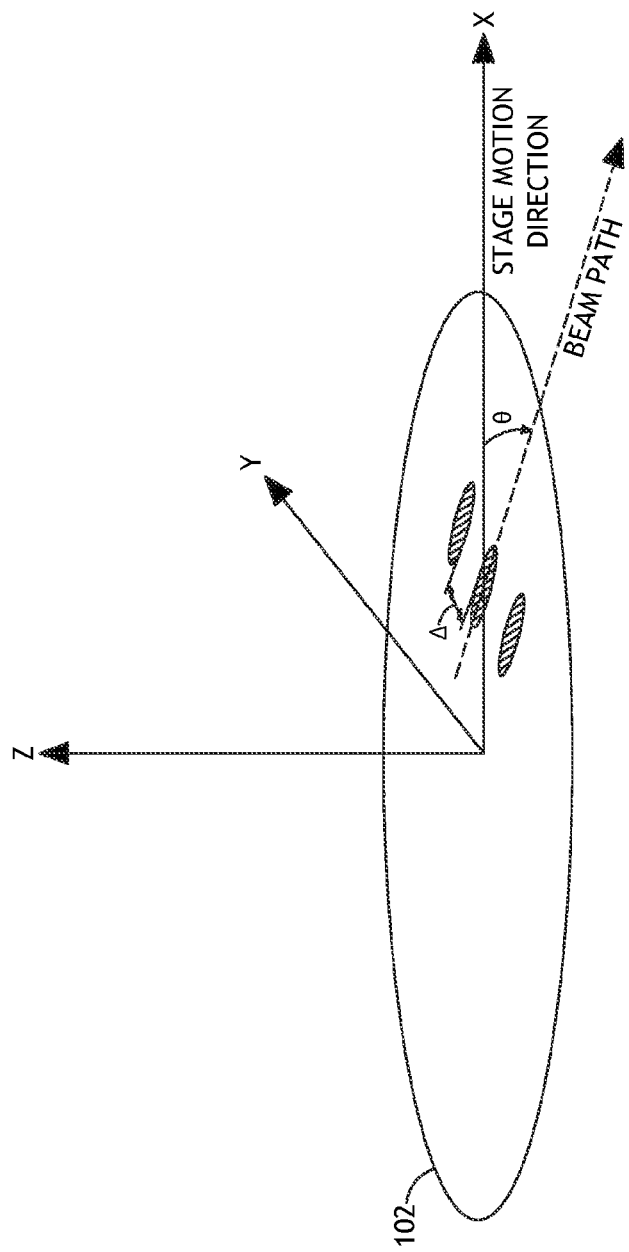
FIG. 1B illustrates motion of a sample relative to a plurality of illumination beams impinging upon a surface of the sample, in accordance with an embodiment of this disclosure.

FIG. 1B illustrates a plurality of beam spots on a surface of the sample 102 with an XYZ coordinates provided for reference, where the lateral actuator 106 is configured to translate the sample 102 along the X-axis. In some embodiments, it is advantageous to illuminate the sample with a plurality of spots disposed along the X-axis. However, configuring the illumination optics to generate such a MS pattern poses implementional challenges in an oblique incidence angle due to much smaller depth of focus (DOF). This combination of small DOF and high bandwidth due to fast spin rate is very challenging for autofocus system (AFS) design.

If beams travel within the XZ plane at oblique angle, beam waist size can be maintained within a reasonable range, but creating a tilted focus plane relative to beam waist plane is technically difficult. Accordingly, it is advantageous to provide beams along a tilted angle θ relative to X-axis, where the beams travel in the plane defined by Z-axis and the beam path, as illustrated in FIG. 1B. In some embodiments, the tilt angle θ is typically ranged from 0 to 50 degrees of the X-axis so that spot size along the beam path is not stretched too much, thereby maintaining match between the radial spot size and the pitch size.

In some embodiments, the allowable scan pitch depends on spot-to-spot separation Δ and tilt angle θ, and may be determined according to the following formulas:

$$p_m = \frac{n}{m} \times \Delta \sin\theta$$

$$p = \frac{p_m}{n} = \frac{1}{m} \times \Delta \sin\theta$$

where p is the sampling pitch, $p_m$ is the mechanical pitch, n is the number of spots, m is an integer that does not share the common divisor with n, Δ is the spot separation, and θ is the tilt angle. Thus as long as θ is not 90 degrees, a set of allowable pitch sizes can be used in inspection. The spin rate can be adjusted for given throughput or sensitivity target.

However, pitch error may result from spot separation along the tangential direction. Because spots are not located along the X-axis, spots sitting disposed at different Y positions travel slightly different distances along the radial direction from one revolution to the next. As a result, pitch size cannot be maintained as a constant when scanning from the center of the sample 102 to edge. Instead the spots may follow a very complicated pattern, and pitch error may increase when closer to the center of the sample 102. The maximum pitch error depends upon spot separation Δ, tilt angle θ, and radial position r. In some embodiments, the pitch error for a given position can be approximated according to the formula:

$$\delta(r_0, \Delta, \theta) \approx \frac{(\Delta \cos\theta)^2}{2r_0}$$

where δ is the pitch error at radial position $r_o$. The exact pitch error follows a much more complicated but predictable form.

Pitch error may be oversampling or undersampling depending on position of a scanned track of the sample 102. Pitch error can exacerbate sizing error and lead to higher false counts if not handled properly. Sizing error can be handled algorithmically. However, false counts may result in unrecoverable loss in throughput for a given sensitivity target. Pitch error due to spot placement can be very large. If corrected pitch size is used to re-construct the defect signal, a much higher boost factor may exist for an undersampled region, leading to an increase in false defect count and degraded sensitivity. One method of reducing pitch error is uneven spot separation. Oversampling in regions with large undersampling may further mitigate false counts due to excessive pitch error. For example, the system 100 may be configured to scan regions associated with high pitch error at a smaller scanning pitch. As illustrated in FIGS. 2 through 5, the system 100 may be configured for controlling scan pitch, spot size, spot separation, and/or spin rate to compensate pitch error resulting from tangential spot separation.

Figure 2:
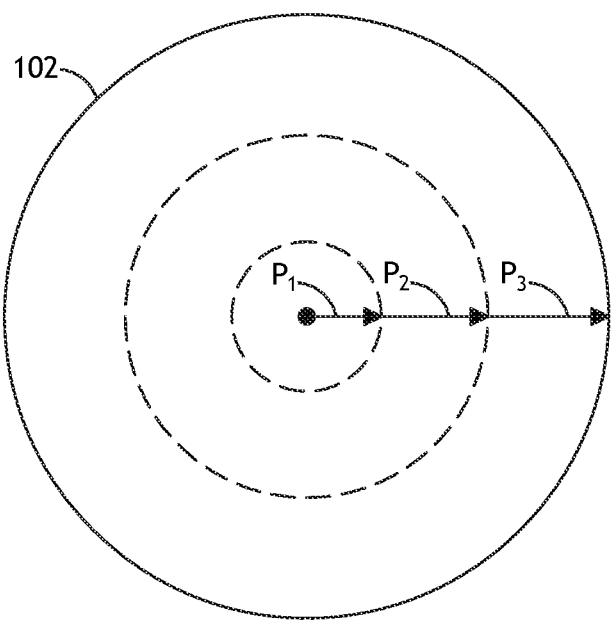
FIG. 2 illustrates a plurality of zones on a surface of a sample, each zone associated with a respective scan pitch, in accordance with an embodiment of this disclosure.

As illustrated in FIG. 2, the system 100 may be configured to scan the sample 102 according to multiple pitch size zones. For example, the lateral actuator 106 may be configured to translate the sample 102 along the X-axis according to at least a first (smaller) scan pitch in regions with large pitch error such as central portions of the sample 102, and a second (larger) scan pitch in regions with lower error rates such as outer portions of the sample 102. In the exemplary embodiment illustrated in FIG. 2, three pitch zones may cover the sample 102. The sample 102 may be scanned according to nominal scan pitch ($P_3$) at the outermost region, 2× nominal pitch ($P_2$) in the middle region, and 4× nominal pitch ($P_1$) in the innermost region near the center of the sample 102. The foregoing example is illustrative of multi-zone scanning; however, the number of zones and respective scan pitches are arbitrary and may vary according to requirements of a specific implementation. For example, it may be advantageous to provide additional zones towards the center of the sample 102.

Proper care needs to be taken so that proper sampling is maintained at the zone boundary, including overlap between zones. In some embodiments, illustrated in FIG. 2, sequentially scanning across the sample 102 with multiple pitch sizes provides good timing performance and is easy to implement. In other embodiments, it may be advantageous to scan each zone twice (i.e. left side to center and center to right side) for increased accuracy. In some embodiments, a central portion (e.g. 2 mm at the center) of the sample 102 may be excluded from the scan to further avoid error.

In some embodiments, the computing system 122 is further configured to determine defect information utilizing a subset of all spots near the center of the sample 102. It may be advantageous to ignore the spots that generate large pitch error. For example, in a 9-spot system, the computing system 122 may be configured to use data from all 9 spots when scanning an outer portion of the sample 102. Whereas, the computing system 122 may be configured to use only data from 3 spots closest to the pattern center when scanning a central portion of the sample 102. Since tangential separation between the 3 spots is much smaller than the entire 9 spots, pitch error may be further reduced.

Figure 3:
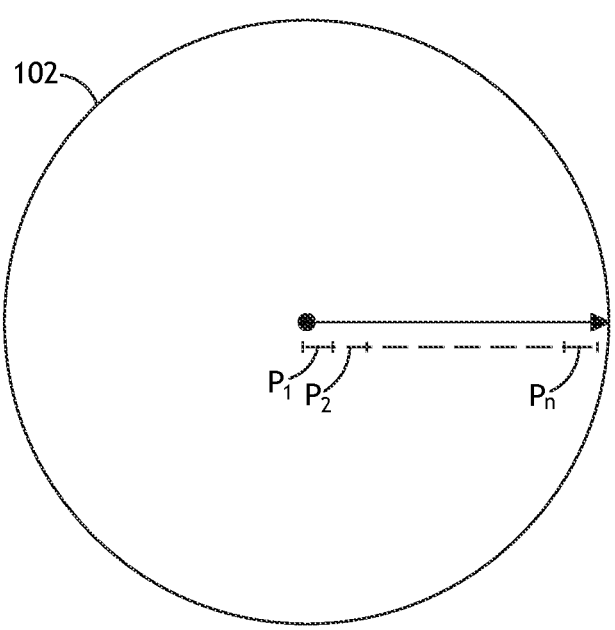
FIG. 3 illustrates substantially continuous variation of scan pitch along a surface a sample, in accordance with an embodiment of this disclosure.

In another embodiment, illustrated in FIG. 3, the system 100 may be configured to scan at least a portion of the sample 102 with a substantially continuously variable scan pitch. To maintain proper sampling, the scan pitch may be continuously or discretely determined according to the spot separation Δ and tilt angle θ. In some embodiments, the scan pitch is determined according to allowable pitch size utilizing the following formula:

$$p_m = \frac{n}{m} \times \Delta \sin\theta$$

$$p = \frac{p_m}{n} = \frac{1}{m} \times \Delta \sin\theta$$

as previously described above. For an illumination layout that adjusts Δ or θ during scan, the lateral actuator 106 may be configured to translate the sample 102 at adjusted velocity to match to allowable pitch size during the scan. In some embodiments, the system 100 is configured to use smaller nominal pitch so that total error (nominal+max pitch error) is maintained within a selected error threshold. Thus, signal-to-noise ratio (SNR) over the entire sample 102 can be kept above a specified minimum SNR. Instead of or in addition to controlling scan pitch by changing actuation velocity of the sample 102, the spot array generator 110 may be further configured to control scan pitch. In some embodiments, the spot array generator 110 may include a diffractive optical element coupled to a rotating actuator. The tilt angle θ, thus the allowable scan pitch, may be adjusted by rotating the diffractive optical element in sync with sample translation by the lateral actuator 106.

Figure 4:
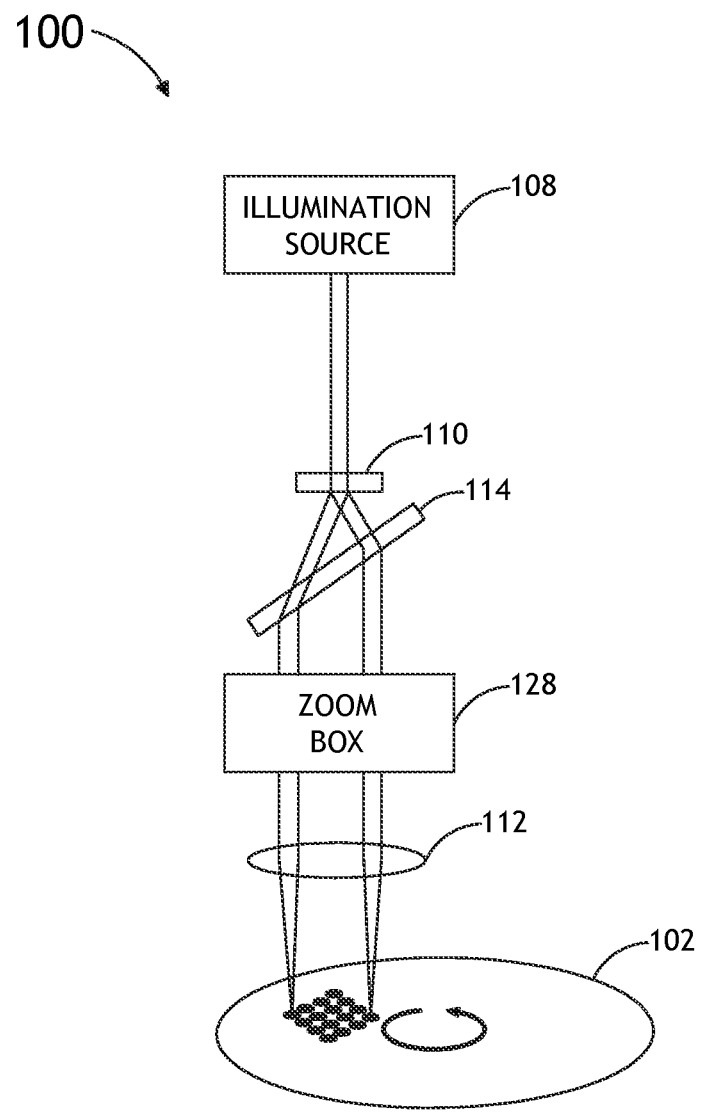
FIG. 4 is a block diagram illustrating a portion of the multi-spot inspection system, wherein the system includes a zoom box for controlling spot size and/or separation, in accordance with an embodiment of this disclosure.

In some embodiments, illustrated in FIG. 4, the system 100 may further include a zoom box 128 disposed along the illumination path. The zoom box 128 (e.g. zooming lens assembly) may be configured to control the ratio of spot separation to spot size. For example, the zoom box 128 may be configured to maintain the ratio below a selected threshold. When switching throughput mode, the zoom box 128 may be configured to zoom spot size and spot separation while the ratio is kept small in order to keep a low ratio of pitch error to pitch size.

Figure 5:
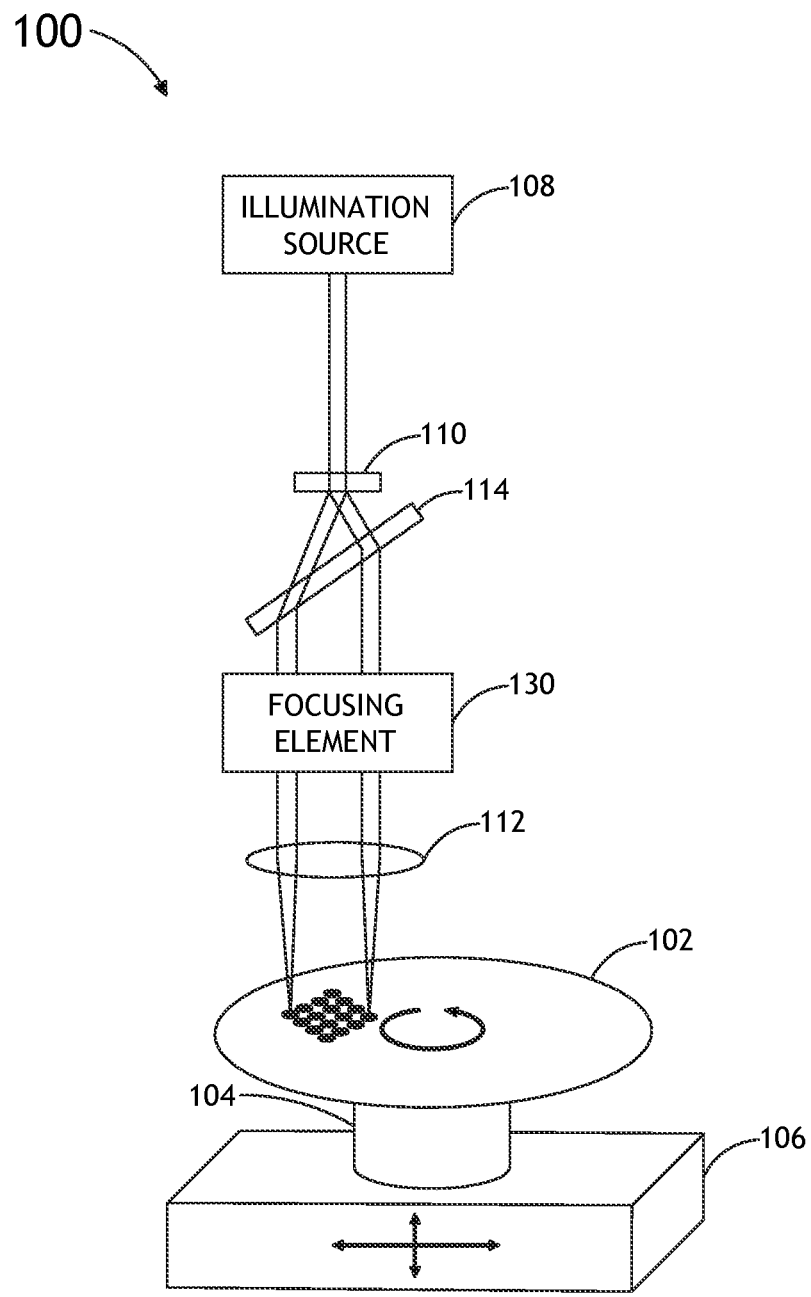
FIG. 5 is a block diagram illustrating a portion of the multi-spot inspection system, wherein the system includes a focusing element for controlling spot size, in accordance with an embodiment of this disclosure.

In some embodiments, illustrated in FIG. 5, the system 100 may further include a focusing element 130 (e.g. focusing lens) disposed along the illumination path. The focusing element 130 may be configured to adjust focus of illumination beams flowing to the surface of the sample 102 to control spot size. Alternatively or in addition to the focusing element 130, the spot size (and focus) may be controlled by actuating the sample 102 upwards or downwards along the Z-axis. In some embodiments, the stage assembly may further include an actuator configured to move the sample 102 up or down to a selected Z-position. The spot size may be adjusted during a scan so that at least a first (larger) spot size is used near the center of the sample 102 and a second (smaller) spot size is used to scan outer portions of the sample 102, thereby maintaining proper coverage over the entire sample 102. This method may be used alone or in combination with slowing down the spin rate near the center of the sample 102. In some embodiments, the rotating actuator 104 is configured to slow down the spin rate from nominal spin profile when scanning a central portion of the sample 102 to make up for loss of SNR due to pitch error.

Several methods may be employed to match signals from different spots. In some embodiments, the computing system 122 is configured to compensate for different signal bandwidth between different spots. The difference in signal bandwidth arises because of a slight difference in the angle between spinning trajectory and spot trajectory. This effect is larger when close to the center of the sample 102. As result, signals collected by the computing system 122 with a certain bandwidth may have different amplitudes depending on which spots the signals come from. The computing system 122 may be configured to compensate the foregoing effect in processing with a proper amplification factor, or by utilizing different bandwidth filters to process signals from different spots.

To properly detect a defect, the peak signal may need to be reconstructed from signals on multiple tracks surrounding the defect. Neighboring tracks are generally associated with different spots. Because the angle between spinning trajectory and spots are slightly different, there is an angular offset between signals from neighboring tracks for a given defect in most cases. In some embodiments, the computing system 122 is further configured to account for this angular offset in order to reconstruct peak signal properly.

The computing system 122 may be further configured to match signal from different spots according to one or more of the following techniques. In some embodiments, the computing system 122 may be configured to measure peak power intensity of each spot, and normalize signals received from various spots accordingly. In some embodiments, the computing system 122 may be configured to characterize beam shape for each spot. The beam shape for spots can be slightly different. Thus, when a signal from each spot passes data acquisition with a certain bandwidth, the signal may be modulated by a different scaling factor due to mismatch between signal bandwidth and data collection bandwidth. The computing system 122 may be configured to resolve the mismatch by using a respective matching filter for each channel. Thus the modulation to signal amplitude is the same of all signals. In some embodiments, the computing system 122 may be configured to measure intensity off a scattering standard sample, and adjust gains of detectors for each spot until measurement signal matches.

Determining peak signal from data on multiple sampling tracks may require determination of the true pitch size. Pitch size may be calculated during runtime. Thus, deterministic pitch error due to spot placement can be accounted with a proper algorithm executing by the computing system 122. In addition to pitch error, several other factors may need to be accounted for in the algorithm to enable sizing accuracy. The signal on sample tracks may be normalized according to the bandwidth difference. Because spots are placed at different tangential positions, illumination spots on different sample tracks cross particle at different angle relative to the direction of linear velocity. This difference depends on radial position of illumination on the surface of the sample 102. Signal matching algorithms executed by the computing system 122 may reduce sizing error in defect inspection.

Beam position noise (BPN) between the sample surface and illumination spot can also generate a positioning error. This error needs to be controlled for a MS system to a tighter level (scaled by 1/n, where n is number of laser spots). For a given spin profile and given throughput, the mechanical pitch $p_m$ may be fixed. Since the sample pitch is $p=p_m/n$, for the MS system 100, the sampling pitch is generally smaller than sampling pitch in a single-spot system for given a throughput. As result, the same BPN results in much bigger relative error in sample pitch size. The main impact of BPN is to increase width of measured size distribution. Some defects having a measured size below the inspection threshold, may be lost accordingly.

The BPN affecting the inspection may result from the relative displacement between illumination beams and sample position. In some embodiments, the computing system 122 is configured to characterize BPN based upon scattering from defects. For example, the computing system 122 may be configured to detect deviation from the beam profile due to BPN. In some embodiments, the computing system 122 may be configured to determine and account for BPN accordingly.

Figure 6A:
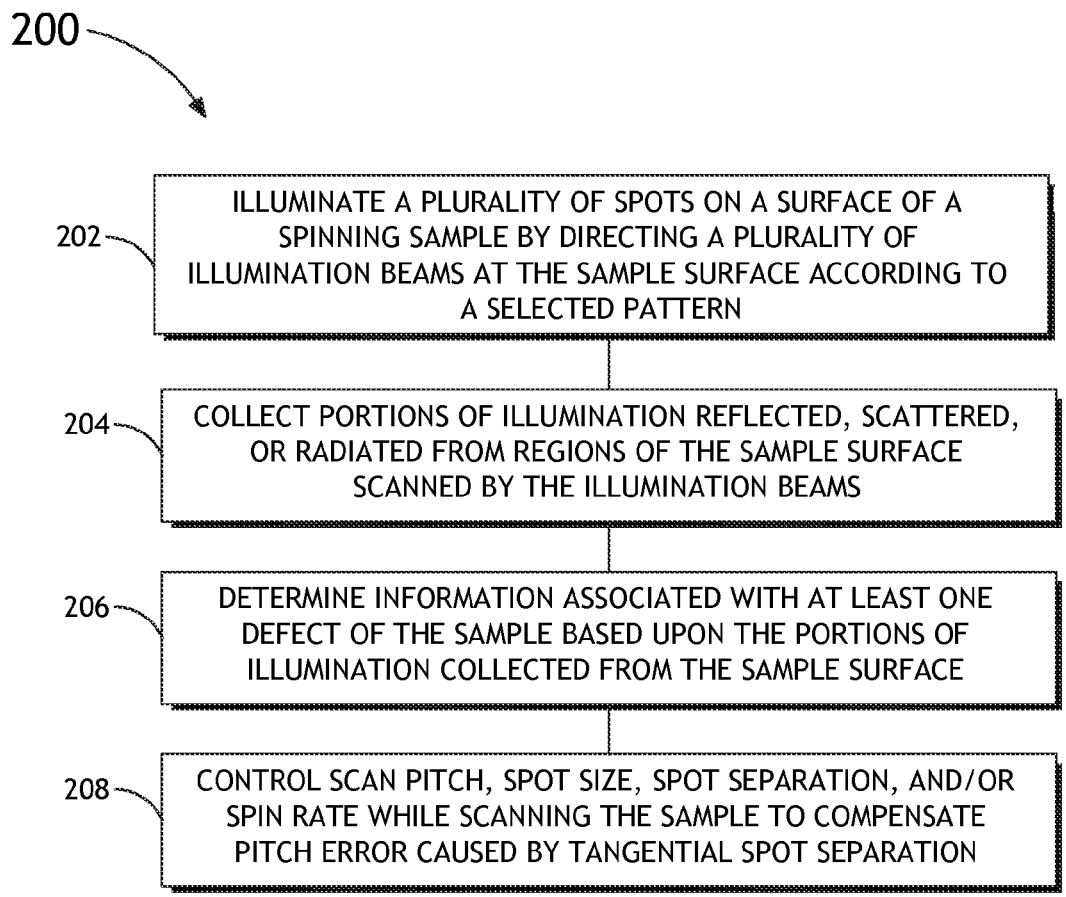
FIG. 6A is a flow diagram illustrating a method of inspecting a sample, in accordance with an embodiment of this disclosure.
Figure 6B:
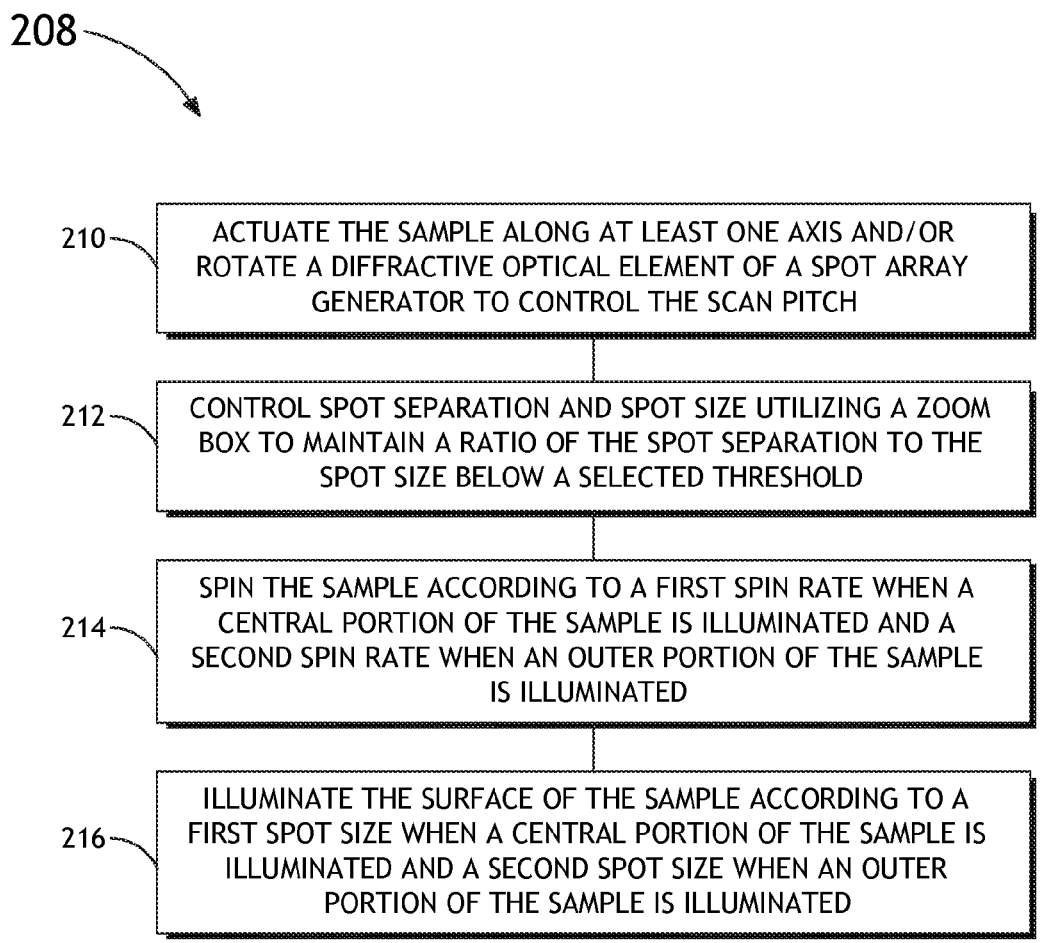
FIG. 6B is a flow diagram illustrating a portion of the method including one or more steps for controlling scan pitch, spot size, spot separation, and/or spin rate to compensate pitch error caused by tangential spot separation, in accordance with an embodiment of this disclosure.

FIGS. 6A and 6B are flow diagrams illustrating a method 200 of inspecting a sample in accordance with system 100. It is noted, however, that one or more steps of method 200 may be accomplished by additional or alternative means beyond those described with regard to the foregoing embodiments of system 100. Accordingly, the method 200 should be construed to encompass any means for carrying out the following steps. Furthermore, the method 200 may include one or more steps for carrying out various functions described with regard to system 100. The following steps are illustrative of an embodiment and are not intended to be in any way limiting.

At step 202, a plurality of spots are illuminated on the surface of the spinning sample 102. In some embodiments, an illumination beam is split into a plurality of beams to generate a selected spot pattern such as, but not limited to, a tangential or radial spacing. At step 204, an array of detectors 120 receives illumination reflected, scattered, or radiated from the illuminated spots as the sample 102 is being scanned by the plurality of beams. At step 206, scan data collected by the detector array 120 is processed to determine information, such as location, size, and/or classification, of at least one defect of the sample 102 based upon the portions of illumination received by the detectors 120 from each spot on the sample 102. At step 208, scan pitch, spot size, spot separation, and/or spin rate may be controlled while the sample 102 is being scanned (i.e. during steps 202 through 206) to compensate pitch error due to tangential spot separation.

In some embodiments, step 208 includes sub-step 210 of actuation the sample 102 at one or more stage velocities along the X-axis to control scan pitch according to multiple pitch zones or substantially continuously varied scan pitch based upon spot separation and tilt angle of the illumination beams. In some embodiments, step 208 includes sub-step 212 of controlling spot separation and spot size by zooming to maintain the ratio of spot separation to spot size below a selected threshold. In some embodiments, step 208 includes sub-step 214 of spinning the sample according to at least a first (lower) spin rate when scanning a central portion of the sample 102 and second (higher) spin rate when scanning an outer portion of the sample 102. In some embodiments, step 208 includes step 216 of illuminating the sample 102 with at least a first (larger) spot size when scanning a central portion the sample 102 and a second (smaller) spot size when scanning an outer portion of the sample 102.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for inspecting a sample, comprising:
    a stage assembly configured to support a sample, the stage assembly including at least one of a rotating actuator or a lateral actuator;
    at least one illumination source configured to provide illumination along an illumination path to a surface of the sample;
    a spot array generator disposed along the illumination path, the spot array generator configured to direct portions of illumination according to a selected pattern to illuminate a plurality of spots within one or more pitch zones of a plurality of pitch zones of the surface of the sample;
    at least one detector array configured to receive illumination reflected, scattered, or radiated from the plurality of spots on the surface of the sample; and
    a computing system in communication with the at least one detector array, the computing system configured to:
        determine information associated with at least one defect of the sample based upon the illumination received by the at least one detector array; and
        controllably adjust at least one of scan pitch, spot size, spot separation, or spin rate based on the one or more pitch zones containing the plurality of spots to compensate pitch error due to tangential spot separation.

2. The system of claim 1, wherein the at least one lateral actuator is configured to actuate the sample along at least one axis to control the scan pitch of the portions of illumination directed at the surface of the sample.

3. The system of claim 2, wherein the at least one lateral actuator is further configured to actuate the sample according to a first scan pitch when a first pitch zone of the sample is illuminated and a second scan pitch when a second pitch zone of the sample is illuminated.

4. The system of claim 2, wherein the at least one lateral actuator is further configured to actuate the sample according to a substantially continuously variable scan pitch based upon spot separation and tilt angle of the portions of illumination directed at the surface of the sample.

5. The system of claim 4, wherein the substantially continuously variable scan pitch is determined according to the following equation:

$$p_m = \frac{n}{m} \times \Delta \sin\theta$$

where
n is the number of spots,
m is an integer value,
$\Delta$ is the spot separation, and
$\theta$ is the tilt angle.

6. The system of claim 1, further comprising:
    a zoom box configured to maintain a ratio of the spot separation to the spot size below a selected threshold.

7. The system of claim 1, wherein the at least one rotating actuator is configured to control the spin rate of the sample, wherein the at least one rotating actuator is further configured to spin the sample at a first spin rate when a central pitch zone of the sample is illuminated and at a second spin rate when an outer pitch zone of the sample is illuminated, wherein the first spin rate is lower than the second spin rate.

8. The system of claim 1, further comprising:
    at least one focusing element configured to control the spot size of the portions of illumination directed at the surface of the sample, wherein the at least one focusing element is further configured to provide a first spot size when a central pitch zone of the sample is illuminated and a second spot size when an outer pitch zone of the sample is illuminated, wherein the first spot size is larger than the second spot size.

9. The system of claim 1, wherein the spot array generator includes a diffractive optical element.

10. The system of claim 9, further comprising:
    at least one rotating actuator coupled to the diffractive optical element, wherein the at least one rotating actuator is configured to rotate the diffractive optical element to control scan pitch of the portions of illumination directed at the surface of the sample.

11. The system of claim 1, wherein the computing system is further configured to determine a relationship between at least two of scan pitch, spot size, spot separation, or spin rate for compensation of pitch error.

12. A system for inspecting a sample, comprising:
    a stage assembly configured to support a sample, the stage assembly including a rotating actuator and a lateral actuator;
    at least one illumination source configured to provide illumination along an illumination path to a surface of the sample;
    a spot array generator disposed along the illumination path, the spot array generator configured to direct portions of illumination according to a selected pattern to illuminate a plurality of spots within one or more pitch zones of a plurality of pitch zones on the surface of the sample;

a zoom box configured to control a separation-to-size ratio of the plurality of spots;

at least one detector array configured to receive illumination reflected, scattered, or radiated from the plurality of spots on the surface of the sample; and a computing system in communication with the at least one detector array, the computing system configured to:

determine information associated with at least one defect of the sample based upon the illumination received by the at least one detector array; and adjust at least one of the lateral actuator, the rotating actuator, the spot array generator or the zoom box to control at least one of scan pitch, spin rate, spot size or spot separation based on the one or more pitch zones containing the plurality of spots to compensate pitch error due to tangential spot separation.

13. The system of claim 12, wherein the lateral actuator is configured to actuate the sample according to a first scan pitch when a first pitch zone of the sample is illuminated and a second scan pitch when a second pitch zone of the sample is illuminated.

14. The system of claim 12, wherein the lateral actuator is configured to actuate the sample according to a substantially continuously variable scan pitch based upon spot separation and tilt angle of the portions of illumination directed at the surface of the sample.

15. The system of claim 14, wherein the substantially continuously variable scan pitch is determined according to the following equation:

$$p_m = \frac{n}{m} \times \Delta \sin\theta$$

where
n is the number of spots,
m is an integer value,
$\Delta$ is the spot separation, and
$\theta$ is the tilt angle.

16. The system of claim 12, wherein the zoom box is further configured to maintain the separation-to-size ratio of the plurality of spots below a selected threshold.

17. The system of claim 12, wherein the rotating actuator is configured to spin the sample at a first spin rate when a central pitch zone of the sample is illuminated and at a second spin rate when an outer pitch zone of the sample is illuminated, wherein the first spin rate is lower than the second spin rate.

18. The system of claim 12, further comprising:
at least one focusing element configured to control spot size of the portions of illumination directed at the surface of the sample, the at least one focusing element further configured to provide a first spot size when a central pitch zone of the sample is illuminated and a second spot size when an outer pitch zone of the sample is illuminated, wherein the first spot size is larger than the second spot size.

19. The system of claim 12, wherein the spot array generator includes a diffractive optical element.

20. The system of claim 19, further comprising:
at least one rotating actuator coupled to the diffractive optical element, the at least one rotating actuator configured to rotate the diffractive optical element to control scan pitch of the portions of illumination directed at the surface of the sample.

21. The system of claim 12, wherein the computing system is further configured to determine a relationship between at least two of scan pitch, spot separation, spot size, or spin rate for compensation of pitch error.

22. A method of inspecting a sample, comprising:
directing portions of illumination according to a selected pattern to illuminate a plurality of spots within one or more pitch zones of a plurality of pitch zones on a surface of a spinning sample;

receiving illumination reflected, scattered, or radiated from the plurality of spots on the surface of the sample;

determining information associated with at least one defect of the sample based upon the illumination received from the surface of the sample; and adjusting at least one of scan pitch, spot size, spot separation, or spin rate based on the one or more pitch zones containing the plurality of spots to compensate pitch error due to tangential spot separation.

23. The method of claim 22, wherein adjusting at least one of scan pitch, spot size, spot separation, or spin rate includes:
actuating the sample along at least one axis to control the scan pitch of the portions of illumination directed at the surface of the sample.

24. The method of claim 23, further comprising:
actuating the sample according to a first scan pitch when a first pitch zone of the sample is illuminated; and
actuating the sample according to a second scan pitch when a second pitch zone of the sample is illuminated.

25. The method of claim 23, further comprising:
actuating the sample according to a substantially continuously variable scan pitch based upon spot separation and tilt angle of the portions of illumination directed at the surface of the sample.

26. The method of claim 25, wherein the substantially continuously variable scan pitch is determined according to the following equation:

$$p_m = \frac{n}{m} \times \Delta \sin\theta$$

where
n is the number of spots,
m is an integer value,
$\Delta$ is the spot separation, and
$\theta$ is the tilt angle.

27. The method of claim 22, wherein adjusting at least one of scan pitch, spot size, spot separation, or spin rate includes:
maintaining a ratio of the spot separation to the spot size below a selected threshold utilizing a zoom box.

28. The method of claim 22, wherein adjusting at least one of scan pitch, spot size, spot separation, or spin rate includes:
spinning the sample according to a first spin rate when a central pitch zone of the sample is illuminated; and
spinning the sample according to a second spin rate when an outer pitch zone of the sample is illuminated, wherein the first spin rate is lower than the second spin rate.

29. The method of claim 22, wherein adjusting at least one of scan pitch, spot size, spot separation, or spin rate includes:
controlling the spot size of the portions of illumination directed at the surface of the sample according to a first spot size when a central pitch zone of the sample is illuminated; and
controlling the spot size of the portions of illumination directed at the surface of the sample according to a second spot size when an outer pitch zone of the sample is illuminated, wherein the first spot size is larger than the second spot size.

30. The method of claim 22, wherein adjusting at least one of scan pitch, spot size, spot separation, or spin rate includes:
rotating a diffractive optical element to control scan pitch of the portions of illumination directed at the surface of the sample.

31. The method of claim 22, wherein the adjusting at least one of scan pitch, spot size, spot separation, or spin rate includes determining a relationship between at least two of scan pitch, spot separation, spot size, or spin rate for compensation of pitch error.

* * * * *